(12) United States Patent
Nishino et al.

(10) Patent No.: US 8,618,503 B2
(45) Date of Patent: Dec. 31, 2013

(54) ELECTRON BEAM STERILIZER

(75) Inventors: Yukinobu Nishino, Kanazawa (JP); Tokuo Nishi, Kanazawa (JP); Yukihiro Yamamoto, Kanazawa (JP)

(73) Assignee: Shibuya Kogyo, Ltd., Kanazawa-shi, Ishikawa (JP)

( * ) Notice: Subject to any disclaimer, the term of this patent is extended or adjusted under 35 U.S.C. 154(b) by 126 days.

(21) Appl. No.: 12/451,535

(22) PCT Filed: May 20, 2008

(86) PCT No.: PCT/JP2008/059209
§ 371 (c)(1),
(2), (4) Date: Nov. 16, 2009

(87) PCT Pub. No.: WO2008/146654
PCT Pub. Date: Dec. 4, 2008

(65) Prior Publication Data
US 2010/0123090 A1    May 20, 2010

(30) Foreign Application Priority Data

May 31, 2007    (JP) ................. 2007-144440

(51) Int. Cl.
*A61L 2/08* (2006.01)
*G21K 5/02* (2006.01)
(52) U.S. Cl.
USPC ............ 250/455.11; 250/453.11; 250/454.11; 250/492.1; 250/492.2; 250/492.3
(58) Field of Classification Search
USPC .................. 250/492.1, 492.3, 453.11, 454.11, 250/455.11; 422/22; 414/783, 754
See application file for complete search history.

(56) References Cited

U.S. PATENT DOCUMENTS

| 5,607,045 | A | 3/1997 | Kronseder |
| 6,717,161 | B1 | 4/2004 | Cekic et al. |
| 2005/0158218 | A1 | 7/2005 | Dumargue et al. |
| 2007/0018115 | A1 | 1/2007 | Naka et al. |
| 2008/0296398 | A1* | 12/2008 | Hickman et al. ............ 239/8 |

FOREIGN PATENT DOCUMENTS

| EP | 1 736 174 | 12/2006 |
| EP | 1 736 174 A1 | 12/2006 |
| JP | 8-169422 | 7/1996 |
| JP | 11-1212 | 1/1999 |
| JP | 11-19190 | 1/1999 |
| JP | 11-137645 | 5/1999 |
| JP | 2002-211520 | 7/2002 |
| JP | 2006-6726 | 1/2006 |
| JP | 2007-29709 | 2/2007 |
| JP | 2003-192095 | 7/2009 |

* cited by examiner

*Primary Examiner* — Phillip A Johnston
*Assistant Examiner* — Hanway Chang
(74) *Attorney, Agent, or Firm* — Flynn, Thiel, Boutell & Tanis, P.C.

(57) ABSTRACT

An electron beam sterilizer has a bottle holder 28 provided with a rotation shaft 38, a neck gripper 70 mounted to a lower end of the rotation shaft 38, a rotating body 30 for rotating and moving the neck gripper 70 and a rotator revolver (segment gear 54, pinion gear 46, disc-shaped cam 66, etc.), and while conveying the resin bottle 2 in the state of being held, the resin bottle 2 is sterilized by irradiation with the electron beam through the irradiation window 19 of the electron beam irradiation device 18. The entire surface of the resin bottle 2 is completely sterilized by being rotated by the rotator during the movement in front of the irradiation window 19 and, thereafter, the rotator is inverted in position to return the neck gripper to thereby discharge the bottle.

2 Claims, 5 Drawing Sheets

ELECTRON BEAM STERILIZER

TECHNICAL FIELD

The present invention relates to an electron beam sterilizer for sterilizing a vessel, which is being conveyed, by being irradiated with an electron beam and, more particularly, to an electron beam sterilizer capable of sterilizing an entire peripheral surface of a vessel during the passing of the vessel in front of an irradiation window formed into an electron beam irradiation device.

BACKGROUND TECHNOLOGY

There have been known electron beam sterilizers, having various structures, for sterilizing vessels by irradiating the vessels with an electron beam generated from an electron beam irradiation device during the conveyance of the vessels being held by vessel holding means (for example, refer to Patent Document 1 to Patent Document 4).

A sterilizer for sterilizing a vessel with an electron beam disclosed in the above Patent Document 1 is provided with an electron beam generation section, a sterilization processing chamber including an electron beam irradiation window of the electron beam generation section, vessel conveying means for conveying the vessel to be processed in a vertical orientation from an inlet portion of the sterilization processing chamber to an outlet portion thereof, and rotation imparting means for imparting rotation to the vessel during a time at which the vessel has a position just before reaching the electron beam irradiation window of the electron beam generation section to a time at which the vessel has completely passed in front of the irradiation window.

The rotation imparting means is composed of a lateral pair of endless belts disposed to press side surfaces of a neck portion of the vessel from both sides. One of the endless belts has a rotating speed higher than that of the other one of the endless belt, and based on such a difference in the rotating speeds of both the endless belts, the rotation is imparted to the vessel during the conveyance thereof.

An electron beam sterilizer disclosed in the Patent Document 2 includes conveying means having tow wires, by which a mouth portion of the vessel is clamped and the vessel is conveyed in a vertically suspended state, and when the vessel passes an irradiation space of an irradiation chamber, an electron beam irradiating means irradiates the vessel with the electron beam from side surfaces of the vessel. In the electron beam irradiating time, rotating means operates two wires so as to rotate the vessel around a central axis thereof by at least 25 degrees.

An electron beam sterilizer for sterilizing a plastic hollow vessel disclosed in the Patent Document 3 is provided with an orbit (circulation) mechanism for vacuum-sucking and then fixing a bottom portion of a plastic hollow vessel supplied from a supply mechanism and circulating the fixed plastic hollow vessel, and an electron beam irradiation mechanism for irradiating the circulating plastic hollow vessel with the electron beam, and an interval maintaining mechanism capable of maintaining constant an interval between the electron beam irradiation mechanism and the plastic hollow vessel.

A vessel sterilizer disclosed in the Patent Document 4 is provided with a plurality of vessel holding means arranged around a rotary body in a circumferential direction thereof at an equal interval, and each of the vessel holding means has two holding portions so as to hold two vessels side by side in the vertical direction. The rotary body is formed with a conveying path in which an inverting area and a standing conveying area are formed. Inverting means for rotating the vessel holding means around a tangential axial direction as a center of rotation is disposed in the position inverting area, and an electron beam irradiation device is disposed in the standing conveying area.

The vessel held by the vessel holding portion of the vessel holding means is irradiated with the electron beam at the electron beam irradiating position in the standing conveying area, and thereafter, the vessel is inverted in the inverting area in the vertical orientation thereof, at which one surface of the vessel opposite to the surface which has been irradiated with the electron beam is directed to the electron beam irradiation device side. In this orientation, the vessel again receives the electron beam irradiation, thereby completely sterilizing the entire surface of the vessel.

Patent Document 1: Japanese Patent Laid-open Publication No. HEI 11-1212
Patent Document 2: Japanese Patent Laid-open Publication No. HEI 11-19190
Patent Document 3: Japanese Patent Laid-open Publication No. HEI 11-137645
Patent Document 4: Japanese Patent Laid-open Publication No. 2007-29709

DISCLOSURE OF THE INVENTION

Problem to be Solved by the Invention

With the structure of the Patent Document 1, there is a fear that an interval between adjacent vessels in conveyance thereof may become unstable and a travelling speed of the vessel may also be unstable, resulting in scattering of the irradiation conditions, and moreover, the structure of the Patent Document 1 is unsuitable for speed-up requirement.

Furthermore, with the structure of the Patent Document 2, there also is a fear that an interval between adjacent vessels in the conveyance thereof may become unstable and a travelling speed of the vessel may also be unstable, resulting in the scattering of the irradiation conditions, and moreover, the structure of the Patent Document 2 is unsuitable when requiring an operation speed-up.

With the structure of the Patent Document 3, since the bottom surface of the vessel is vacuum-sucked, this bottom portion is not sterilized and thus is inconvenient.

With the structure of the Patent Document 4, it is required to provide a number of grippers (vessel holding means), which requires a great number of parts or members to be disposed, thus providing a problem and, moreover, since two vessels are conveyed side by side in a vertical orientation, it is required for the device to have an increased height, resulting in an increase in its entire size.

Means for Solving the Problem

The invention is an electron beam sterilizer for sterilizing a bottle made of a resin by being irradiated with an electron beam generated from an electron beam irradiation means during the conveyance of the bottle while being held by a bottle holding means, wherein
the bottle holding means is provided with a rotation shaft having an axis extending in the same direction as a central axis of the held resin bottle and a gripper mounted to one end of the rotation shaft and adapted to hold the resin bottle by clamping a neck portion of the resin bottle from both sides thereof, moving means that circularly moves the rotation shaft of the bottle holding means, and rotating means that rotates the rotation shaft around the axis thereof are provided, and the resin bottle held by the gripper is rotated by a predetermined angle by rotating the rotation shaft in front of the electron beam irradiation means that irradiates the resin bottle with the electron beam and, thereafter, the resin bottle is inverted in position by the predetermined angle to thereby release the resin bottle from the gripper.

The invention is also characterized in that there are arranged bottle supply means that pushes the resin bottle to the moving gripper from a direction substantially perpendicular to the rotation shaft and bottle discharge means that pulls out the resin bottle from the moving gripper in a direction substantially perpendicular to the rotation shaft, and the electron beam irradiation means is arranged along a bottle conveying path extending from a supply position at which the resin bottle is pushed into the gripper by the bottle supply means to a discharge position at which the resin bottle is pulled out by the bottle discharge means.

Furthermore, the invention is characterized in that the resin bottle is rotated by an angle more than 90 degrees by the rotation of the rotation shaft.

Further, the invention is characterized in that the moving means is provided with a rotating body supporting the rotation shafts at an equal interval in a circumferential direction of the rotating body, the rotation shafts being circularly moved by rotating the rotating body, and the electron beam irradiation means is provided with a plurality of irradiation windows through which the electron beam is emitted, the irradiation windows being arranged at different angles respectively along the conveying path of the rotating body.

Effect of the Invention

In the electron beam sterilizer of the present invention, the rotation shafts to which grippers holding the bottles are circularly moved, rotated by a predetermined angle in front of the irradiation window of the electron beam irradiation means, and thereafter, reversely rotated (inverted in position) to thereby discharge the bottles, so that the bottles can be stably conveyed, and during the conveyance, the entire outer surface of the vessel can be completely sterilized. Moreover, the structure of the sterilizer can be simplified and made compact.

Figure 1:
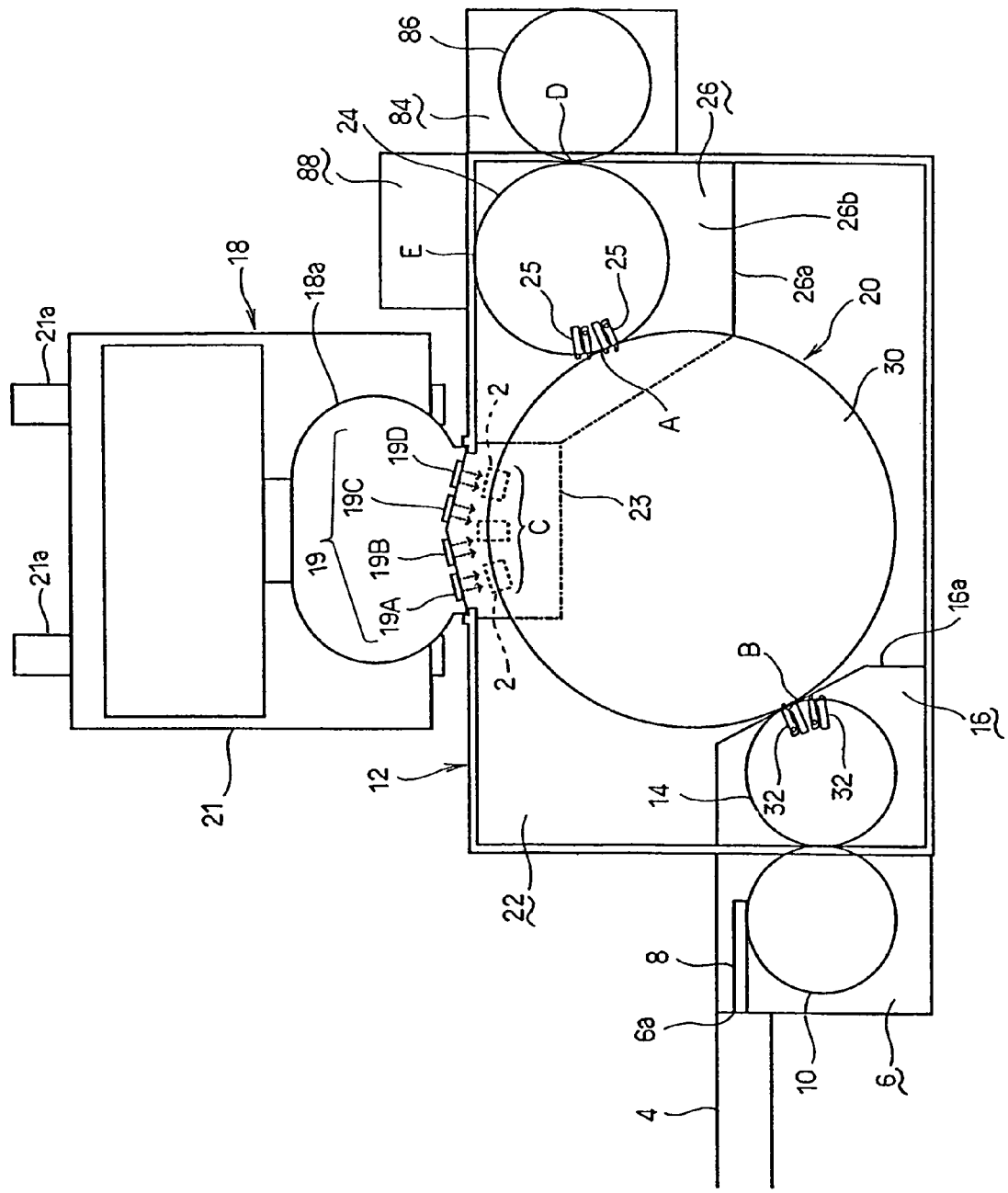
FIG. 1 is a plan view schematically showing an entire configuration of an electron beam sterilizer (Embodiment 1).

EXPLANATION OF REFERENCE NUMERALS 2 resin bottle
18 electron beam irradiating means (electron beam irradiation device)
19 irradiation window
28 bottle holding means
30 moving means (rotating body)
38 rotation shaft
46 rotating means (pinion gear)
54 rotating means (segment gear)
66 rotating means (disc-shaped cam)
70 gripper (neck gripper)

BEST MODE FOR CARRYING OUT THE INVENTION

Bottle holding means is provided with a rotation shaft and a gripper mounted to one end of the rotation shaft. There are also provided moving means for circularly moving the rotation shaft of the bottle holding means and rotating means for rotating the rotation shaft around a central axis thereof. The structure is made such that the axis of the rotation shaft is positioned on a central axis of a resin-made bottle held by a gripper in a state that a neck portion of the resin bottle is clamped from both sides thereof, the resin bottle held by the gripper is then moved by the moving means, the rotation shaft is rotated by the rotating means to thereby rotate the resin bottle by a predetermined angle and, after the rotation of the predetermined angle, the resin bottle is released from the gripper. According to such a structure, the device can be simplified in structure and, in addition, the entire surface of the resin bottle can be completely sterilized, thus achieving the object of the present invention.

Embodiment 1

Hereunder, the present invention will be explained with reference to an embodiment shown in the accompanying drawings.

Figure 2:
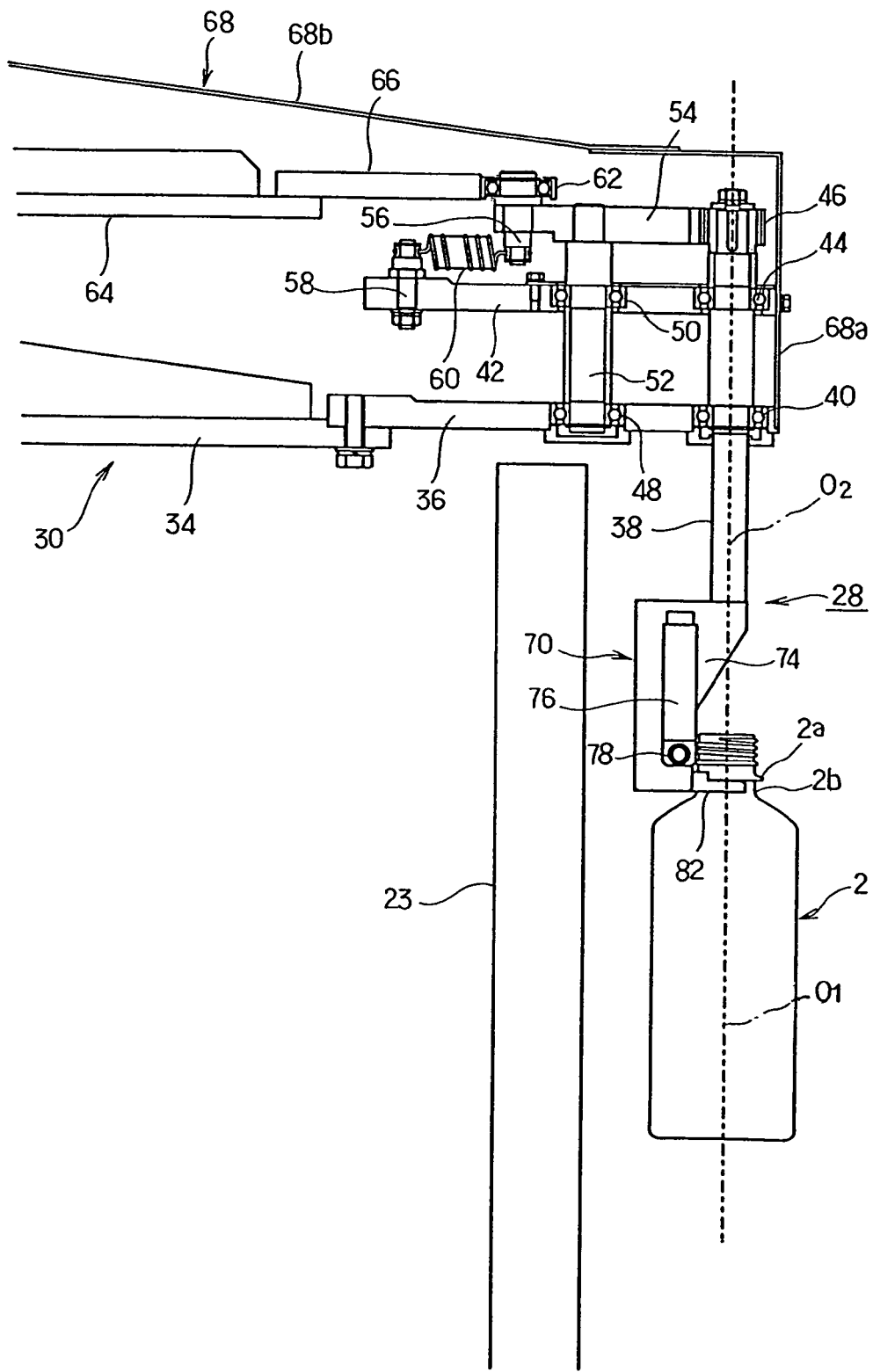
FIG. 2 is an elevational section of bottle holding means provided for the electron beam sterilizer.

A vessel 2 sterilized by an electron beam sterilizer according to this embodiment and, thereafter, filled with an inner content such as a liquid in a subsequent processing is a bottle made of a resin such as a PET bottle (see FIG. 2). The resin bottles 2 are each supported at a lower surface side of a flange portion 2a formed at a neck portion by a support rail of an air conveyer 4 and continuously conveyed from a rear side by blowing air by a propelling blower. The conveyed resin bottles 2 enter an introduction chamber 6 and, thereafter, are separated by an infeed screw 8 at a predetermined interval and then transferred to a rotary wheel 10 in the introduction chamber 6.

A plurality of vessel holding means (not shown) are provided for the rotary wheel 10 in the introduction chamber 6 at predetermined intervals in the circumferential direction thereof, and the resin bottles 2 transferred through the infeed screw 8 are received and then rotated and conveyed. An opening (not shown) through which the resin bottle 2 can pass is formed in a wall surface 6a of the chamber 6 into which the resin bottle 2 is conveyed.

Subsequent to the introduction chamber 6, there is located a sterilization box (sterilization chamber) 12, composed of a lead wall section, for shielding the electron beam or X-ray (braking X-ray) from leaking outside when sterilizing the resin bottle 2 by the electron beam irradiation. An interior of the sterilization box 12 is sectioned into: a supply chamber 16 on the inlet side at which the supply wheel 14 is arranged; a main chamber 22 provided with a rotary-type vessel conveying device 20 in which the resin bottle 2 received from the supply wheel 14 is conveyed and is moved in front of an electron beam irradiation window 19 of the electron beam irradiation device (irradiator) mentioned hereinafter; and a discharge chamber 26 in which a discharge wheel 24 receiving the resin bottle 2 sterilized by the irradiation with the electron beam from the electron beam irradiation device and then discharging the resin bottle 2 is disposed.

An opening, not shown, enabling the resin bottle 2 to pass therethrough is formed at a portion at which the resin bottle 2 is transferred to the supply wheel 14 in the supply chamber 16 from the rotary wheel 10 of the introduction chamber 6. The supply wheel 14 receiving the resin bottle 2 from the rotary wheel 10 in the introduction chamber 6 transfers the resin bottle 2 to the vessel conveying device 20 in the main chamber 22. An opening, not shown, is also formed at a partition wall section 16a sectioning the supply chamber 16 and the main chamber 22 for enabling the resin bottle 2 to pass therethrough. The vessel conveying device 20 disposed in the main chamber 22 is provided with a plurality of bottle holding means 28 (refer to FIGS. 2 to 5 explained hereinafter) disposed in the circumferential direction of an outer peripheral portion of the rotating body 30 at equal intervals, respectively. Further, a plurality of vessel holding means 32 are provided, at equal intervals in the circumferential direction, for the supply wheel 14 for receiving the resin bottle 2 from the vessel holding means of the rotary wheel 10 disposed in the introduction chamber 6 and transferring the resin bottle 2 to the bottle holding means 32 of the vessel conveying device 20. This vessel holding means 32 constitutes bottle supply means.

Electron beam irradiation means (electron beam irradiation device) 18 is disposed adjacent to the sterilization box 12 made of lead. This electron beam irradiation device 18 is provided with a vacuum chamber (acceleration chamber) 18a that irradiates the resin bottle 2 with the electron beam and rests on a mount table 21 to be movable on rails 21a. The electron beam irradiation device 18 serves, as is well known, to heat filaments in a vacuum condition in the vacuum chamber 18a to thereby generate thermal electrons, which are then accelerated by a high voltage into a high speed electron beam. The high speed electron beam is taken out into the atmosphere through a metallic window foil, such as Ti, attached to the irradiation window formed to the irradiation section, and an object (article) to be irradiated (resin bottle 2 in this embodiment) positioned within the irradiation area C in front of the irradiation widow is irradiated with the electron beam to be thereby subjected to the sterilization processing.

The electron beam irradiation device 18 of this embodiment has four irradiation windows 19 (19A, 19B, 19C, 19D) continuously formed in the irradiation section. These four irradiation windows 19A, 19B, 19C 19D are arranged on an outer peripheral side of the conveying path of the vessel conveying device 20. In this embodiment, since the conveying path of the vessel conveying device 20 has a circular shape, these four irradiation windows 19A, 19B, 19C 19D are arranged two by two (19A, 19B, and 19C, 19D) with different angles so as to provide an equal distance to the circular conveying path. Further, a beam collector 23 is disposed on a side opposite to the irradiation windows 19 of the electron beam irradiation device 18 with the vessel conveying path being interposed. Since the electron beam irradiation range can be increased along the vessel conveying path by increasing the number of the irradiation windows, the number of the irradiation widows may be increased as occasion demands without limiting to four as in this embodiment. The arrangement thereof may be also changed without necessarily differing the angles, and they may be arranged linearly.

The electron beam irradiation area C is, as mentioned above, on the front side of the irradiation windows 19 (19A, 19B, 19C, 19D) of the electron beam irradiation device 18. A discharge chamber 26 is formed, by being defined by the wall surface 26a and the ceiling surface 26b, from a position near a position through which the resin bottle 2 conveyed by the vessel conveying device 20 passes the electron beam irradiation area C. The resin bottle 2 subjected to the electron beam irradiation in the electron beam irradiation area C is transferred to the discharge wheel 24 disposed in the discharge chamber 26 from the bottle holding means 28 of the vessel conveying device 20. The discharge wheel 24 is provided with a plurality of vessel holding means 25 arranged at an equal interval along the circumferential direction, and the resin bottle 2 held by the bottle holding means 28 of the vessel conveying device 20 is taken out and then discharged by the vessel holding means 25. This vessel holding means 25 constitutes the bottle discharge means.

The structure of the bottle holding means 28 provided for the rotary-type vessel conveying device 20 in the main chamber 22 will be explained hereunder with reference to FIGS. 2 to 5.

The plural bottle holding means 28 are arranged at an equal interval along the circumferential direction of the outer peripheral portion of the circular rotary plate 34 constituting the rotating body 30. A mount plate 36 is fixed to the outer peripheral portion of the circular rotary plate 34, a plurality of rotation shafts 38 are supported at the outer peripheral end of this mount plate 36 to be rotatable through ball bearings 40 at an equal interval along the circumferential direction. The rotary plate 34 and the mount plate 36 are formed to be rotatable in a horizontal plane, and the rotation shafts 38 penetrating the mount plate 36 in the supported manner are directed to the perpendicular direction. The resin bottles 2 are held with their central axes Ol being directed perpendicularly, and the rotation shafts 38 have axes 02 of the same direction as the central axes 01 of the resin bottles 2.

An annular intermediate plate 42 is disposed above the mount plate 36, and each of the rotation shafts 38 extends upward such that the upper portion thereof penetrates the intermediate plate 42. The rotation shaft 38 is supported to be rotatable via a ball bearing 44 with respect to the intermediate plate 42. A pinion gear 46 is mounted to an upper end portion of the rotation shaft 38 extending upward over the intermediate plate 42.

On the inner side in the radial direction of the rotation shaft 38, segment gear support shafts 52 are supported to the mount plate 36 fixed to the outer peripheral portion of the rotary plate 36 and to the intermediate plate 42 disposed above the mount plate 36 to be rotatable through bearings 48 and 50, respectively. Segment gears 54 are fixed to the upper ends of the segment gear support shafts 52. The upper end portion of each of the segment gear support shafts 52 is coupled to substantially the central portion of the segment gear 54, and an engaging tooth 54a (refer to FIG. 3) is meshed with a pinion gear 46 mounted on the rotation shaft 38. Further, a pin 56 directed vertically is attached to an end portion side, of the segment gear 54, directed radially inward of the rotating body 30. A spring 60 is coupled between the lower end of this vertical pin 56 and the upper end of a stand pin 58 disposed most inward side of the intermediate plate 42 so as to always pull the radially inward end of the segment gear 54.

Figure 3:
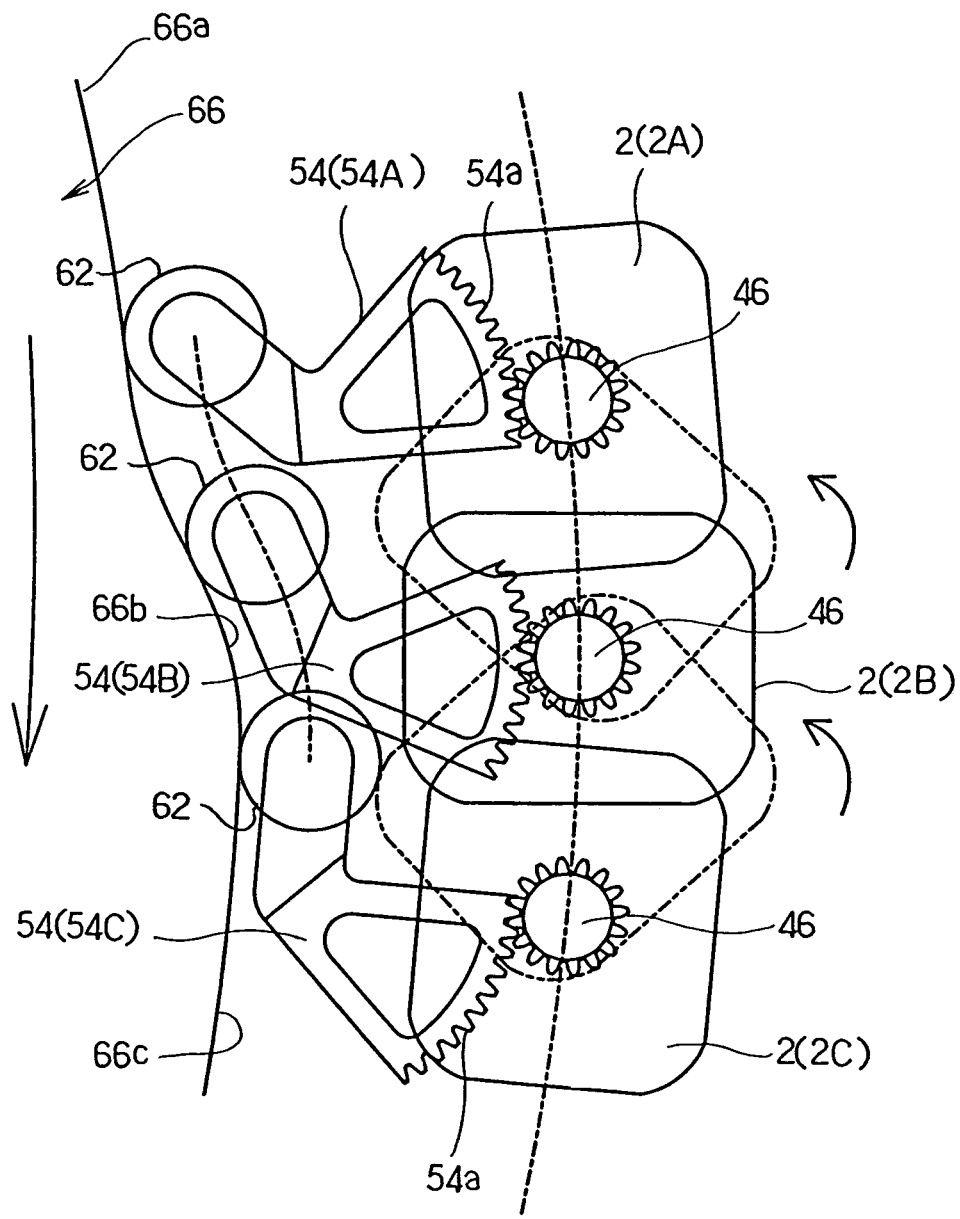
FIG. 3 is a plan view showing a structure of rotating means for rotating a rotation shaft of the bottle holding means.

A cam follower 62 is mounted to the upper end portion of the vertical pin 56 of the segment gear 54. Incidentally, above the rotary plate 34, a stationary disc 64 is disposed, and a disc-shaped cam 66 is mounted to an outer peripheral portion of this stationary disc 64. The cam follower 62 pulled by the spring 60 abuts against an outer peripheral cam surface of the disc-shaped cam 66. Although a portion of the disc-shaped cam 66 is shown in FIG. 3, the disc-shaped cam 66 is formed so as to move, in the irradiation area C positioned in front of the irradiation window 19 of the electron beam irradiation device 18, to a large diameter portion 66c from a small diameter portion 66a through a transfer portion 66b. According to this transferring, the segment gear 54 is rotated in angles from the state that one end (an end positioned on a lower side in FIG. 3) of the engaging tooth 54a is meshed with the pinion gear 54 to the state that the other end (an end positioned on an upper side in FIG. 3) is meshed therewith (refer to the segment gears 54A, 54B, 54C in FIG. 3). According to the rotation of the segment gear 54, the pinion gear 46 is rotated by substantially 180 degrees. Further, this rotation of the pinion gear 46 (rotation of the rotation supporting shaft 38) is not necessarily 180 degrees, and the rotation by at least more than 90 degrees may be accepted.

Furthermore, after the rotation of the segment gear 54 and the pinion gear 46 in front of the irradiation window 19 of the electron beam irradiation device 18, and during a time when the resin bottle 2 reaches the discharge position at which the resin bottle 2 is transferred from the vessel conveying device 20 to the discharge wheel 24, a cam curve described by the disc-shaped cam 66 varies to the small diameter portion 66a from the large diameter portion 66c in a state reverse to the state in the electron beam irradiation area C. According to the shape of this portion of the cam 66, the segment gear 54 rotates reversely by the same angles as the rotating angle at the electron beam irradiation time. Thereafter, the cam curve of the disc-shaped cam 66 accords with the small diameter portion 66a during the movement from the vessel discharge position A to the front portion of the irradiation window 19 via the vessel supply position B. The rotary plate 34, the mount plate 36 disposed on the outer peripheral portion thereof, the intermediate plate 42 disposed above the mount plate 36, the segment gear 54, the pinion gear 46 on the rotation shaft 38, the stationary plate 64 on the stationary side, and the disc-shaped cam 66, which constitute the rotating body 30, are covered by the cover 68 including the peripheral wall 68a and the ceiling wall 68b. Further, the rotating body 30 constitutes moving means for circularly moving the rotation shaft 38, and the pinion gear 46, the segment gear 54, the cam follower 62 and the disc-shaped cam 66 constitute the rotating means of the rotation shaft 38.

Figure 4:
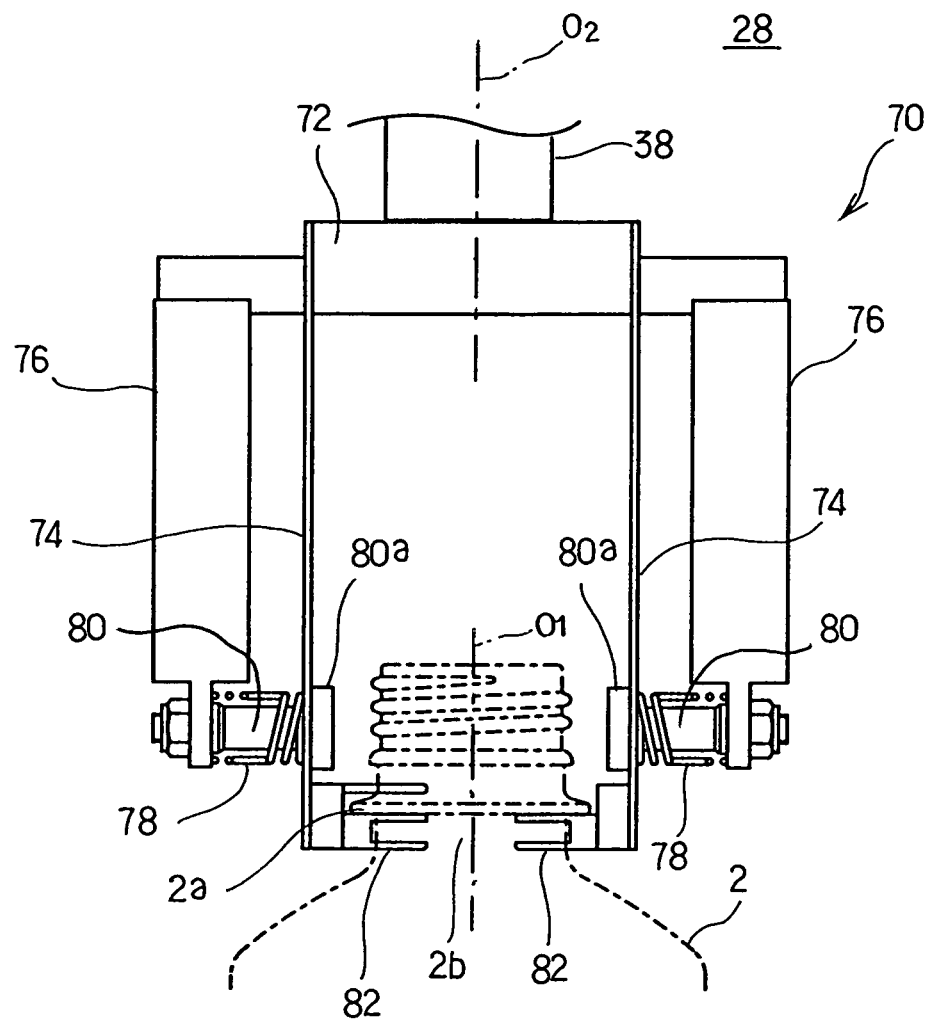
FIG. 4 is a front view of a gripper provided for the bottle holding means.
Figure 5:
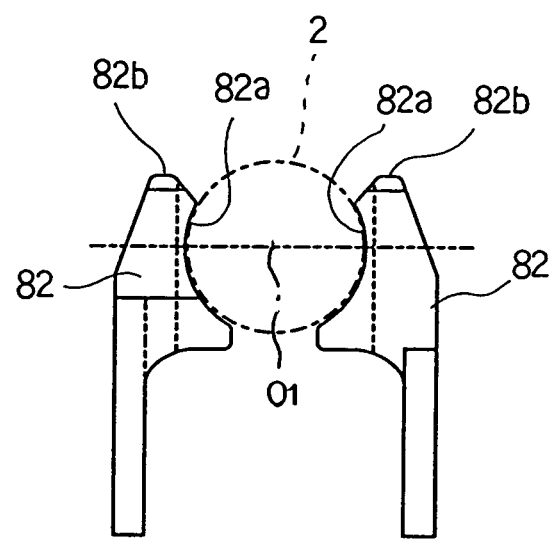
FIG. 5 is a plan view showing a pair of gripping portions of the gripper.

Next, a neck gripper 70 mounted at the lower end of each of the rotation shafts 38 supported in the vertical orientation will be explained with reference to FIG. 2 and FIGS. 4 and 5.

Each of the neck grippers 70 includes two plate springs 74 fixed, perpendicularly in parallel with each other, to both side surfaces of a mount member 72 fixed to the lower end face of each of the rotation shafts 38. Support members 76 are fixed to the mount member 72 outside the plate springs 74 to be parallel therewith. Coil springs 78 are interposed between the plate springs 74 and the front end portions of the support members 76 so as to always urge both the front end portions of the plate springs 74 in a direction approaching each other, and in a usual state, both the front end portions stop in abutment against stoppers (head portions 80a of bolt 80 inserted between the plate springs 74 and the support members 76, respectively,) so as to keep substantially the parallel state. Furthermore, when the front end portions of the plate springs 74 are pushed from their inner surface sides, they are moved in the direction widening from each other against the urging force of the coil springs 78.

Both the plate springs 74 and the support members 76 are disposed to be shifted in positions radially inward of the rotating body 30 with respect to the axial line 02 of the rotation shaft 38. Gripping portions 82 are provided at the lower end portions of the plate springs 74, respectively, in a projecting manner so as to hold the resin bottles 2 on extension lines of the rotation shafts 38, the gripping portions 82 are opposed to each other, and the opposing portions thereof are formed into vertically two plate shapes having front ends each having a recessed surface 82a having a circular shape substantially corresponding to the outer diameter of the neck portion 2b of the resin bottle 2. These gripping portions 82 are circularly moved by the rotating body 30, and the front end portions 82b are directed radially outward at the vessel supply position B to the vessel conveying device 20 and the vessel discharge portion A. At the vessel supply position B, the neck portion 2b of the resin bottle 2 is pushed into the direction perpendicular to the rotation shaft 38 and then held thereby. On the other hand, at the vessel discharge portion A, the resin bottle 2 held by both the gripping portions 82 is pulled out toward the direction of the front end portions 82b of the gripping portions 82 approximately perpendicular to the rotation shaft 38 (radially outward direction of the rotating body 30).

An intermediate chamber 84 is disposed in adjacent to the discharge chamber 26 positioned on the most downstream side within the sterilization box 12. A chamber (not shown) in which a rinser, a filler, etc., are arranged is disposed on the downstream side of the intermediate chamber 84. Within the intermediate chamber 84, a rotary wheel (neck wheel) 86 provided with vessel holding means (not shown) is disposed, and this neck wheel 86 receives the resin bottle 2 from the discharge wheel 24 in the discharge chamber 26, and rotates and conveys the bottle 2, which is thereafter transferred to the supply wheel in the chamber in which the rinser and the filler are disposed. Further, a position denoted by the letter D in FIG. 1 is a transfer position at which the resin bottle 2 is transferred from the discharge wheel 24 in the discharge chamber 26 to the neck wheel 86 of the intermediate chamber 84.

The discharge wheel in the discharge chamber 26 also serves as an intermediate reject wheel, and in a case where it is judged by information from a sensor or like that the resin bottle 2 is normally sterilized, the resin bottle 2 received from the vessel conveying device 20 is transferred to the neck wheel 86 of the next intermediate chamber 84 to be subjected to the next processing. However, in a case where it is judged that the resin bottle 2 has not been irradiated with the electron beam or that the sterilization has not been completely performed, the resin bottle 2 is not transferred to the neck wheel 86 of the intermediate chamber 84 and discharged into a reject chamber 88 disposed adjacent to the sterilization box 12. A position denoted by the letter E in FIG. 1 is a reject position.

An operation of the electron beam sterilizer of the structures mentioned above will be explained hereunder.

Vessels sterilized by this sterilizer and filled with an inner liquid are resin bottles 2, and are conveyed by blowing air by a propelling blower from the rear side of the bottle in a state of being held on the lower surface side of the flange portion 2a formed at the neck portion by support rails (not shown) of the air conveyer 4. The resin bottles 2 conveyed by the air conveyer 4 enter the introduction chamber 6, are separated at a constant interval by the infeed screw 8, and transferred to the vessel holding means of the rotary wheel 10. After the rotation and conveyance by the rotary wheel 10, the resin bottle 2 is transferred to the supply wheel 14 disposed in the supply chamber 16 of the sterilization box 12 made of lead. The resin bottle 2 held by the vessel holding means 32 of the supply wheel 14 is rotated and conveyed, and then transferred to the bottle holding means of the rotary type vessel conveying device disposed within the main chamber 22. The bottle holding means 28 includes the neck gripper 70 mounted to the lower end of each of the rotation shafts 38 arranged perpendicularly, and this neck gripper 70 holds the neck portion 2b formed below the flange portion 2a of the resin bottle 2. The neck gripper 70 has a pair of gripping portions attached to the two plate springs 74, respectively, and the neck portion 2b of the resin bottle 2 is pushed in a space between both the gripping portions 82 from the radially outer side of the rotating body 30. The resin bottle 2 pushed from the front end sides 82b of both the gripping portions 82 is clamped between the recessed portions 82a of both the gripping portions 82 by the spring force of the plate springs 74.

The rotating position of the rotation shaft 38 to which the neck gripper 70 is mounted is determined by engaging the pinion gear 46, which is mounted to the upper end of the rotation shaft 38, with the segment gear 54 which is rotatable in accordance with the cam curve of the disc-shaped cam 66. The cam shape of the disc-shaped cam 66 provides the small diameter portion at the supply position B of the vessel conveying device 20, at which the segment gear 54 has the state denoted by reference numeral 54A shown in FIG. 3. The vessel holding means 28 holding the resin bottle 2 is rotated and moved by the rotation of the rotating body 30, and when the vessel holding means 28 enters the electron beam irradiation area C, the electron beam is emitted through the irradiation windows 19 (19A, 19B, 19C, 19D) of the electron beam irradiation device 18, and the resin bottle 2 is irradiated with the electron beam from the radially outward side of the rotating body 30, i.e., the surface side directed to the irradiation window side. Thereafter, the cam shape of the disc-shaped cam 66 is changed from the small diameter portion 66a to the large diameter portion 66c through the moving portion 66b, and by the rotation of the segment gear 54, the pinion gear 46 meshed with this segment gear 54 is rotated to thereby rotate, approximately by 180 degrees, the rotation shaft 38 and the neck gripper 70 provided at the lower end portion thereof. Then, the resin bottle 2 held by the neck gripper 70 is rotated by 180 degrees during the state 2A in FIG. 3 to the state 2C via the state 2B. As mentioned above, during the passing through the electron beam irradiation area C, the resin bottle 2 is rotated approximately by 180 degrees, and the surface of the bottle 2 facing the radially outer side and the surface thereof facing the radially inner side are changed from each other in their positions, so that the entire outer surface of the resin bottle 2 can be completely sterilized.

Since the front end portions 82b of the gripping portions 82 holding the resin bottle 2 rotated by 180 degrees during the passing through the electron beam irradiation area C are directed radially inward of the rotating body 30, the front end portions 82b are rotated reversely (inverted in position) by the same angles as that at the electron beam irradiation time before reaching the discharge position A. In this reversely rotating area, the cam curve of the disc-shaped cam 66 varies from the large diameter portion 66c to the small diameter portion 66a through the moving portion 66b in the manner reverse to the electron beam irradiation time, and the segment gear 54 is rotated reversely to thereby rotate the rotation shaft 38 and both the gripping portions 82 and the front end portions 82b of the gripping portions 82 are directed radially outward of the rotating body 30.

After the orientation of the neck gripper 70 returns to the state of the vessel supply position B, the resin bottle 2 is held by the vessel holding means 25 of the discharge wheel 24 disposed in the discharge chamber at the discharging position A and pulled out from the neck gripper 70. Thereafter, the resin bottle 2 is transferred to the vessel holding means of the intermediate wheel 86 at the receiving position D and then conveyed to the rinser or filler for subjecting to the next processing. Further, in this embodiment, although the vessel conveying device 20 is provided with the bottle holding means 28 at the peripheral portion of the rotating body 30, the vessel conveying device 20 is not limited to such a rotary type one and, for example, there is adopted a structure in which the conveying means may be mounted to a chain, for example, stretched around a plurality of sprockets. Further, although there was adopted the structure in which the gripper 70 is mounted to the lower end of the rotation shaft 38 to hold the resin bottle 2 in the vertically normally standing orientation with its mouth portion being directed upward, the gripper 70 may be mounted to the upper end of the rotation shaft 38 to hold the resin bottle 2 in the vertically inverted orientation.

The invention claimed is:

1. An electron beam sterilizer for sterilizing a bottle made of resin by being irradiated with an electron beam generated from an electron beam irradiation means during conveyance of a bottle while being held by a bottle holding means, wherein the bottle holding means is provided with a rotation shaft positioned on a central axis of the resin bottle held by the bottle holding means and has an axis extending in a same direction as the central axis of the held resin bottle and a gripper mounted to one end of the rotation shaft and adapted to hold the resin bottle by clamping a neck portion of the resin bottle from both sides thereof by a pair of gripping portions opposed to each other, moving means that circularly moves the rotation shaft of the bottle holding means, rotating means that rotates the rotation shaft around the axis thereof are provided, and the resin bottle held by the gripper is rotated by approximately 180° by the rotation of the rotation shaft of the rotating means on the central axis of the resin bottle by rotating the rotation shaft in front of the electron beam irradiation means that irradiates the resin bottle with the electron beam and, thereafter, the resin bottle is reversely rotated by approximately 180° by the rotating means to thereby release the resin bottle from the gripper at a discharge position, wherein the gripper holds the resin bottle at an extension of the rotation shaft, the resin bottle is pushed into and held in the gripping portions of the gripper at a given supply position, the resin bottle is pulled out and released from the gripping portions of the gripper at a given discharge position, there are arranged bottle supply means that pushes the resin bottle to the moving gripper from a direction substantially perpendicular to the rotation shaft and bottle discharge means that pulls out the resin bottle from the moving gripper in the direction substantially perpendicular to the rotation shaft, the electron beam irradiation means is arranged along a bottle conveying path extending from a supply position at which the resin bottle is pushed into the gripper by the bottle supply means to the discharge position at which the resin bottle is pulled out by the bottle discharge means and the resin bottle is rotated by an angle of substantially 180 degrees by the rotation of the rotation shaft.

2. The electron beam sterilizer according to claim 1, wherein the moving means is provided with a rotating body supporting the rotation shafts at an equal interval in a circumferential direction of the rotating body, the rotation shafts being circularly moved by rotating the rotating body, and the electron beam irradiation means is provided with a plurality of irradiation windows through which the electron beam is emitted, the irradiation windows being arranged at different angles respectively along the conveying path of the rotating body.

* * * * *